United States Patent [19]
Houlihan

[11] 3,987,059
[45] Oct. 19, 1976

[54] 2-SUBSTITUTED INDOLES AND PROCESS FOR THEIR PREPARATION

[75] Inventor: William J. Houlihan, Mountain Lakes, N.J.

[73] Assignee: Sandoz, Inc., E. Hanover, N.J.

[22] Filed: Aug. 25, 1975

[21] Appl. No.: 607,455

Related U.S. Application Data

[63] Continuation-in-part of Ser. No. 477,610, June 10, 1974, abandoned.

[52] U.S. Cl. .................... 260/326.16; 260/319.1; 260/558 R; 260/558 P; 260/562 R; 260/562 A; 424/274
[51] Int. Cl.$^2$ .............. C07D 209/08; C07D 209/12
[58] Field of Search ................... 260/319.1, 326.16

[56] References Cited
FOREIGN PATENTS OR APPLICATIONS
543,846   3/1942   United Kingdom ............. 260/319.1

OTHER PUBLICATIONS
Piozzi et al., "Chem. Abstracts," vol. 60, pp. 9232–9233, (1964).
Bradsher, "Chem. Abstracts," vol. 51, p. 6579(b), (1957).

*Primary Examiner*—Lewis Gotts
*Assistant Examiner*—S. P. Williams
*Attorney, Agent, or Firm*—Gerald D. Sharkin; Robert S. Honor; Thomas O. McGovern

[57] ABSTRACT

Highly branched α-substituted indoles, e.g., 2-(1-methylcyclohexyl)-indole, are prepared by treating N-(α-branched carbonyl) toluidines with alkyl lithium. The reaction sequence may be illustrated as

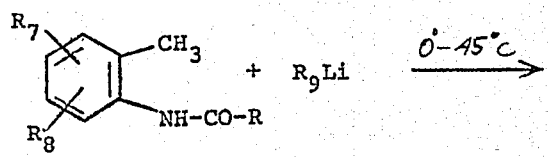

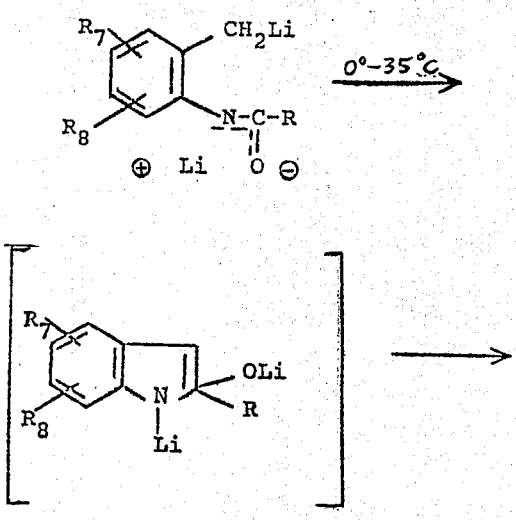

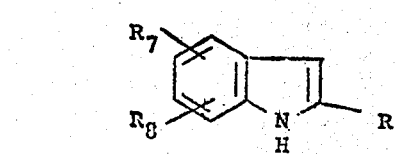

4 Claims, No Drawings

2-SUBSTITUTED INDOLES AND PROCESS FOR THEIR PREPARATION

This application is a continuation-in-part of copending application, Ser. No. 477,610, filed June 10, 1974, and now abandoned This invention relates to highly branched derivatives of indole. In particular, it relates to indoles having highly branched substituents at the 2-position and to a novel process for preparing such compounds in high yields.

The compounds which may be prepared by the process of this invention may be represented by the following structure:

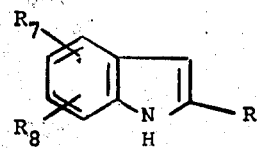

(I)

where R is

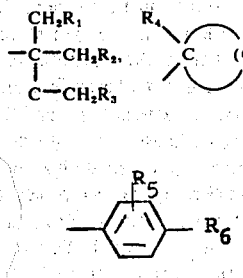

or adamantanyl;
where
n is 4, 5, or 6;
$R_1$, $R_2$, and $R_3$ each independently is hydrogen, methyl or ethyl;
$R_4$ is lower alkyl, i.e., alkyl having 1 to 4 carbon atoms, e.g., methyl, ethyl, isopropyl, isobutyl, and the like;
$R_5$ and $R_6$ each independently is hydrogen, lower alkyl as defined above, lower alkoxy, i.e., alkoxy having 1 to 4 carbon atoms, e.g., methoxy, ethoxy, propoxy, isobutoxy, and the like; or
$R_5$ and $R_6$ together is methylenedioxy and
$R_7$ and $R_8$ each independently is hydrogen, lower alkyl as defined above, lower alkoxy as defined above, or halo having an atomic weight of about 19 to 35, e.g., fluorine or chlorine.
and pharmaceutically acceptable acid addition salts thereof.

The compounds in which R is

where
n and $R_4$ are as defined above,
or one of $R_1$, $R_2$, and $R_3$ are other than hydrogen, are novel. In the preferred cycloalkyl substituted compounds, n is 5 and $R_4$ is methyl. In the preferred aryl substituted compounds $R_5$ and $R_6$ are each independently hydrogen, methyl or methoxy and are preferably adjacent to each other. The preferred significance for $R_7$ and $R_8$ is hydrogen.

The compounds of formula (I) are prepared in accordance with the following reaction scheme:

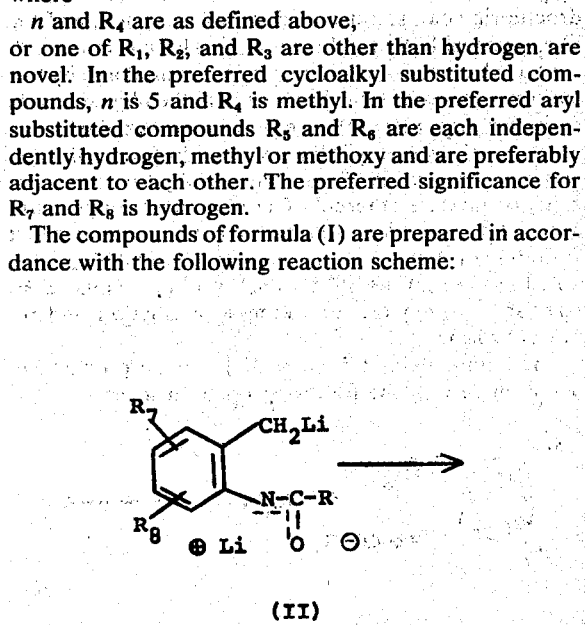

(II)

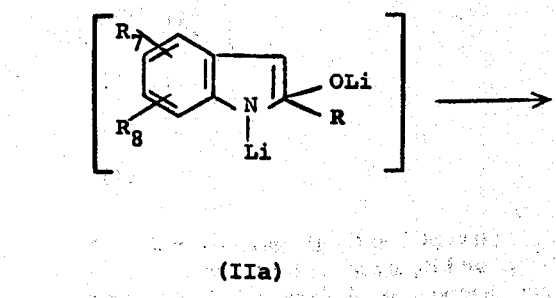

(IIa)

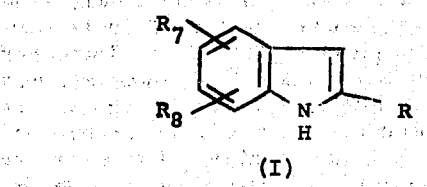

(I)

where R, $R_7$, and $R_8$ are as defined above.

The compounds of formula (I) are prepared by allowing a compound of formula (II) to stand in an inert solvent and in an inert atmosphere for 1 to 48 hours, preferably 15 to 48 hours. After standing, the reaction is quenched with water or an inorganic acid, e.g., hydrochloric acid, sulfuric acid, phosphoric acid and the like, preferably hydrochloric acid. The particular solvent used is not critical, and may be an aliphatic hydrocarbon, such as hexane, heptane, and the like; aromatic hydrocarbons, such as benzene, toluene, and the like or ethers, such as diethyl ether, tetrahydrofuran, dioxane and the like, preferably hexane, tetrahydrofuran, benzene, or mixtures thereof. The particular temperature at which the reaction is carried out is not critical, but it is preferred that it be run between 0° and 45°, preferably between 20° to 25° C. The product is isolated by standard techniques, for example, extraction and recrystallization.

The compounds of formula (II) may be prepared in accordance with the following reaction scheme:

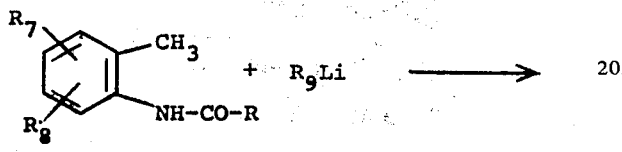

(III)             (IV)

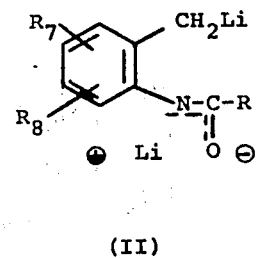

(II)

where
$R_9$ is alkyl of 1 to 6 carbon atoms and
R, $R_7$, and $R_8$ are as defined above.

The compounds of formula (II) are prepared by treating a compound of formula (III) with a compound of formula (IV) in an inert solvent. Although the particular solvent used is not critical, it is preferred that the reaction be run in the same solvents as indicated above for the preparation of the compounds of formula (I). Again, hexane, tetrahydrofuran and benzene, or mixtures thereof are especially preferred. The temperature at which the reaction is run is not critical, but is preferred that the reaction be carried out between about 0° to 35° C, preferably 10° to 25° C. The time of the reaction also is not critical, but it is preferred that the reaction be carried out at a rate which does not cause the temperature of the reaction to rise above 35° C, preferably 25° C. It is further preferred that the reaction be run in an inert atmosphere provided by inert gases such as helium, argon or nitrogen. Nitrogen is especially preferred. The compounds of formula (II) can be isolated by evaporation, but it is preferred that the compound be stored and used as a solution or suspension in an inert solvent such as those indicated above.

The compounds of formula (III) may be prepared in accordance with the following reaction scheme:

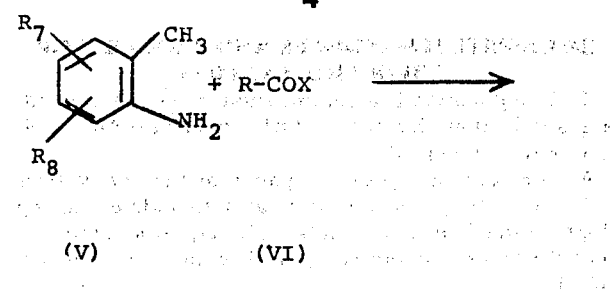

(V)             (VI)

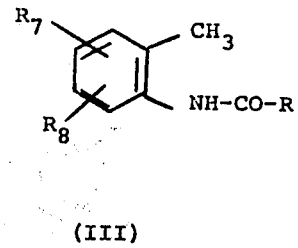

(III)

where
X is chlorine or bromine and
R, $R_7$, and $R_8$ are as defined above.

The compounds of formula (III) are prepared by treating a compound of formula (V) with a compound of formula (VI). Although a solvent is not necessary, it is preferred that the reaction be run in an inert solvent such as benzene, toluene, diethylether, dioxane, tetrahydrofuran and the like. The temperature is not critical, but is preferred that the reaction be run between 20° to 125° C, preferably at the reflux temperature of the reaction medium. The time of the reaction also is not critical, but it is preferred that the process be carried out for 1 to 5 hours, preferably between about 2 to 4 hours. It is also preferred that an acid-binding agent, such as sodium or potassium carbonate, sodium or potassium bicarbonate or a trialkylamine, such as triethylamine be used in the reaction to remove any halogen ion generated. The final product is isolated by conventional techniques, for example, evaporation and recrystallization.

Many of the compounds of formulae (IV), (V), and (VI) are also known and may be prepared by conventional techniques. The compounds of formulae (IV), (V), and (VI) not specifically described in the literature may be prepared by analogous methods using known starting materials.

The compounds of formula (II) and the compounds of formula (III) in which R is other than phenyl are novel and are included as part of this invention. The compounds of formula (II) can exist in two tautomeric forms having the following structure:

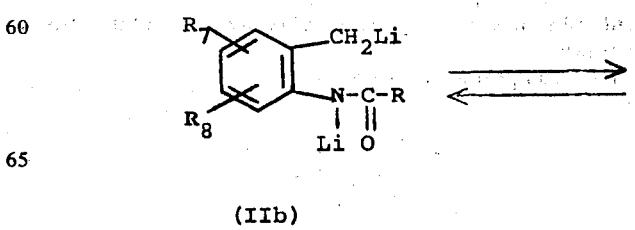

(IIb)

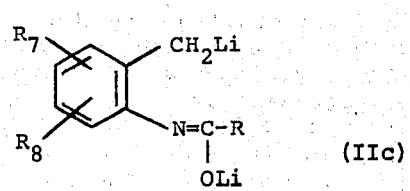

where
R, $R_7$, and $R_8$ are as defined above.
Both forms of the compounds of formula (II) are included in this invention.

The compounds of formula (I), in which R is

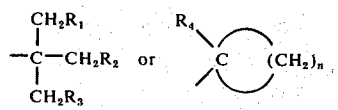

where $n$, $R_1$, $R_2$, $R_3$ and $R_4$ are as defined above, are useful because they possess pharmacological activity in animals. In particular, the compounds are useful as anti-inflammatory agents, as indicated by their activity in rats dosed orally with 10 to 100 mg/kg. of the compound using the acute carrageenan-induced edema procedure substantially as described by Winter (Proc. Soc. Exptl. Biol., 111: 544, 1962) or as indicated by plethysmographic measurement of food volumes on mature Lewis strain rats made arthritic by a single 0.1ml. injection of complete Freunds Adjuvant and dosed orally for 14 days with the compound of formula (I) at a daily dosage rate of 50 mg/kg.

The anti-inflammatory effective dosage for the compounds will depend on the particular compound employed, the method of administration and the severity of the condition being treated. In general, satisfactory results are obtained when these compounds are administered in the treatment of inflammation at a daily dosage of about 10 milligrams to about 200 milligrams per kilogram of animal body weight. This daily dosage is preferably administered 2 to 4 times a day, or in sustained release form. For most large mammals, such as primates, the total daily dosage is from about 600 milligrams to about 3,000 milligrams. Dosage forms suitable for internal use comprise from about 150 milligrams to about 1,500 milligrams of the active compound in intimate admixture with a solid or liquid pharmaceutically acceptable carrier or diluent.

The compounds of formula (I) in which R is adamantyl or

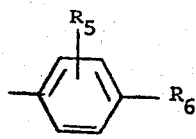

where $R_5$ and $R_6$ are as defined above, are useful as antimicrobial agents as indicated in conventional serial dilution tests by their activity at concentrations of 1 to 100 micrograms per milliliter in vitro against the following organisms:

*Haem. Escherichia coli*
*Salmonella typhimurium*
*Staphylococcus albus* 5226
*Escherichia coli* (120)

Although the anti-microbial effective dosage utilized will vary depending upon the compound employed and the mode of administration, in general, satisfactory results are obtained when these compounds are administered orally or parenterally for systemic use at a daily dosage of about 4 mg. to about 200 mg. per kilogram of animal body weight. This daily dosage is preferably administered 2 to 4 times a day, or in sustained release form. For most large mammals in need of said treatment the total internal daily dosage is from about 250 mg. to about 2.5 gms. Dosage forms suitable for internal use comprise about 62.5 milligrams to about 1250 milligrams of active compound in intimate admixture with a solid or liquid pharmaceutically acceptable carrier or diluent.

The preferred pharmaceutical compositions from the standpoint of preparation and ease of administration are tinctures, ointments, and creams used in topical administration containing from about 0.5 to 30% preferably 0.5 to 10% by weight of the active ingredient.

For such usage, the compounds of formula (I) may be combined with a pharmaceutically acceptable carrier or adjuvant, and may be administered orally in such forms as tablets, capsules, elixers, suspensions and the like, or parenterally in the form of an injectable solution or suspension. The antimicrobial compounds may be administered topically. Topical formulations are prepared by methods well known in the art and the active ingredient may be dissolved or dispersed in water, alcohol, oils, and waxes along with other ingredients such as dispersing agents, stabilizers, fragrances, coloring agents and the like commonly used in tinctures, ointments and creams. These pharmaceutical preparations may contain up to about 90% of the active ingredient in combination with the carrier or adjuvant.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly, are included within the scope of the invention. Representative of the acid addition salts are the mineral acid salts, such as the hydrochloride, hydrobromide, sulfate, phosphate and the like and organic salts, such as the succinate, benzoate, acetate, p-toluenesulfonate, benzenesulfonate, and the like.

A representative formulation suitable for oral administration 2 to 4 times a day in the treatment of inflammation is a capsule prepared by standard encapsulating techniques which contain the following:

| Ingredients | Weight |
| --- | --- |
| 2-(1-methylcyclohexyl)-indole | 100 mg. |
| Inert solid diluent (starch, lactose, kaolin) | 200 mg. |

A water soluble ointment for treatment of topically disposed anti-microbial infection is prepared by standard techniques and contains the following ingredients:

| | Weight (g.) |
| --- | --- |
| Polyethylene glycol (M.W. 4000) | 4000 |
| Polyethylene glycol (M.W. 400) | 800 |

| | Weight (g.) |
|---|---|
| 2-(1-adamantyl)-indole | 100 |

The compounds of formula (I) in which R is

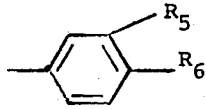

where $R_5$ and $R_6$ are as defined above, are also useful in the preparation of 1-dialkyl-aminoalkyl derivatives which have analgesic properties as described in British Patent 959,203 and in preparing Tryptamine analogs (Chem. Ind., London. 1964, p. 1388).

EXAMPLE 1

2-(1-methylcyclohexyl)-indole

Step A N-(1-methylcyclohexylcarbonyl)-o-toluidine

A mixture of 32.7 grams (0.203 moles) of 1-methyl-1-cyclohexanecarboxylic acid chloride, 15.2 grams (0.11 mole) of anhydrous potassium carbonate and 21.8 grams (0.203 mole) of o-toluidine in 260 ml. of dry toluene is stirred and refluxed for 2.5 hours. The inorganic salts are removed by filtration and the filtrate is concentrated in vacuuo. The residue yields from diethyl ether-pentane 40.5 grams (87%) of N-(1-methylcyclohexyl carbonyl)-o-toluidine; m.p. 138° C.

Following the above procedure but using an equivalent amount of
a. pivaloyl chloride;
b. 1-adamantanoyl chloride;
c. benzoyl chloride;
d. p-toluoyl chloride;
e. p-anisoyl chloride or
f. 3,4-methlenedioxybenzoyl chloride
in place of the 1-methyl-1-cyclohexane carboxylic acid chloride there is obtained
a. N-pivoloyl-o-toluidine (m.p. 112° C);
b. N-(1-adamantanylcarbonyl)-o-toluidine (m.p. 189° C);
c. N-benzoyl-o-toluidine (m.p. 142°–143° C);
d. N-(p-toluoyl)-o-toluidine;
e. N-(p-anisoyl)-o-toluidine or
f. N-(3,4-methylenedioxybenzoyl)-o-toluidine, respectively.

When the above process is carried out using an equivalent amount of benzoyl chloride in place of the 1-methyl-1-cyclohexanecarboxylic acid chloride and in place of the o-toluidine an equivalent amount of:
g. 4-chloro-o-toluidine or
h. 4-methoxy-o-toluidine
there is obtained.
i. N-benzoyl-4-chloro-o-toluidine or
j. N-benzoyl-4-methoxy-o-toluidine, respectively.

Step B 2-(1-methylcyclohexyl)-indole

A flask equipped with a thermometer, stirrer and dropping funnel is immersed in an ice bath, blanketed with nitrogen and then charged with 300ml. of dry tetrahydrofuran and 34.7 grams (0.15 mole) of N-(1-methylcyclohexylcarbonyl)o-toluidine. The stirred solution is treated dropwise with 215 ml. of n-butyllithium in hexane (0.2 mole of n-butyllithium) at such a rate that the internal temperature does not exceed 25° C. After the addition is completed (20 minutes) the cooling is removed and the mixture is stirred for about 18 hours at room temperature. The mixture is cooled in an ice bath and treated dropwise with 150 ml. of 2N hydrochloric acid (pH 2 at end) and then with 150 ml. of benzene. The organic layer is separated, and dried with magnesium sulfate. After filering and concentrating in vacuuo, 37.2 grams of oil is obtained, which is crystallized from pentane to give 24.1 grams (76%) of 2-(1-methylcyclohexyl)-indole; m.p. 50°.

Following the above procedure but using an equivalent amount of
a. N-pivolyl-o-toluidine;
b. N-(1-adamantanylcarbonyl)-o-toluidine
c. N-benzoyl-o-toluidine;
d. N-(p-toluoyl)-o-toluidine;
e. N-(p-anisoyl)-o-toluidine;
f. N-(3,4-methylenedioxybenzoyl)-o-toluidine;
g. N-benzoyl-4-chloro-o-toluidine or
h. N-benzoyl-4-methoxy-o-toluidine
in place of the N-(1-methylcyclohexylcarbonyl)-o-toluidine, there is obtained.
a. 2-t-butylindole (65 to 87% yield); m.p. 71°–72° C;
b. 2-(1-adamantanyl)-indole (59 to 60% yield), m.p. 48° C;
c. 2-phenylindole (70 to 89% yield), m.p. 187°–188° C;
d. 2-(p-toly)-indole;
e. 2-(p-anisyl)-indole;
f. 2-(3,4-methylenedioxyphenyl)-indole;
g. 5-chloro-2-phenylindole (94% yield), m.p. 195°–196° C., or
h. 5-methoxy-2-phenylindole (80% yield), m.p. 148°–149° C., respectively.

What is claimed is:

1. A process for preparing a compound of the formula:

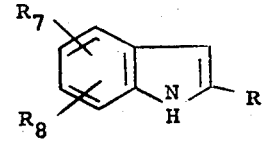

where R is a radical selected from the group consisting of

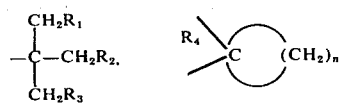

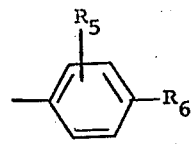

or adamantanyl;
where
 n is 4, 5, or 6
 $R_1$, $R_2$, and $R_3$ each independently is hydrogen, methyl, or ethyl;
 $R_4$ is lower alkyl;

$R_5$ and $R_6$ each independently is hydrogen, lower alkyl, lower alkoxy or $R_5$ and $R_6$ together is methylenedioxy and $R_7$ and $R_8$ each independently is hydrogen, lower alkyl, lower alkoxy, fluorine or chlorine which comprises the steps of:

a. reacting a compound of the formula

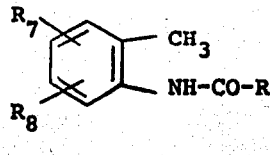

with a compound of the formula:

$R_9Li$ where $R_9$ is alkyl of 1 to 6 carbon atoms in an inert solvent at a temperature of about 0° to 45° C. to form an intermediate of the formula:

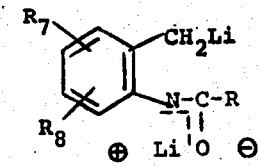

and b. thereafter allowing said intermediate to stand in an inert solvent at a temperature of about 0° to 35° C. and in an inert atmosphere for 1 to 48 hours.

2. A process according to claim 1 in which step (a) is carried out at a temperature of about 20° to 25° C.

3. A process according to claim 1 in which step (b) is carried out at a temperature of about 10° to 25° C.

4. A process according to claim 1 in which $R_7$ and $R_8$ hydrogen.

* * * * *